US009851350B2

(12) United States Patent
Yamamoto

(10) Patent No.: US 9,851,350 B2
(45) Date of Patent: Dec. 26, 2017

(54) NANOHOLE SENSOR CHIP WITH REFERENCE SECTIONS

(71) Applicant: Noriaki Yamamoto, Foster City, CA (US)

(72) Inventor: Noriaki Yamamoto, Foster City, CA (US)

(73) Assignee: KONICA MINOLTA LABORATORY U.S.A., INC., San Mateo, CA (US)

(*) Notice: Subject to any disclaimer, the term of this patent is extended or adjusted under 35 U.S.C. 154(b) by 615 days.

(21) Appl. No.: 14/357,548

(22) PCT Filed: Nov. 21, 2012

(86) PCT No.: PCT/US2012/066397
§ 371 (c)(1),
(2) Date: May 9, 2014

(87) PCT Pub. No.: WO2013/089996
PCT Pub. Date: Jun. 20, 2013

(65) Prior Publication Data
US 2014/0349278 A1    Nov. 27, 2014

Related U.S. Application Data

(60) Provisional application No. 61/570,212, filed on Dec. 13, 2011.

(51) Int. Cl.
*G01N 21/552* (2014.01)
*G01N 33/543* (2006.01)
*G01N 33/553* (2006.01)

(52) U.S. Cl.
CPC ..... *G01N 33/54373* (2013.01); *G01N 21/554* (2013.01); *G01N 33/553* (2013.01)

(58) Field of Classification Search
None
See application file for complete search history.

(56) References Cited

U.S. PATENT DOCUMENTS 7,612,883 B2    11/2009 Que et al.
2008/0278728 A1    11/2008 Tetz et al.
(Continued)

FOREIGN PATENT DOCUMENTS

WO    2008039212    4/2008
WO    2008136734    11/2008
(Continued)

OTHER PUBLICATIONS

International Search Report in the parent PCT application No. PCT/US2012/066397, dated Feb. 11, 2013.
(Continued)

*Primary Examiner* — Rebecca L Martinez
(74) *Attorney, Agent, or Firm* — Chen Yoshimura LLP

(57) ABSTRACT

A device and method for detecting and assessing the quantity of a biological, biochemical, or chemical analyte in a test sample using a simple light source and the naked eye are disclosed. In one embodiment, the device comprises a nanohole sensor chip with two sections, the first of which is a test section, upon which capture agents for a particular analyte are immobilized, and the second of which is a reference section, upon which capture agents conjugated with known quantities of the analyte are immobilized. In another embodiment of the invention, a nanohole sensor chip with a test section and a plurality of reference sections is disclosed. The sensor utilizes light intensity changes exhibited by Fano resonances in the nanoholes for detection of analytes, and allows comparison between the light inten-
(Continued)

sity changes between the reference sections and the test sections for assessing the quantity of the analyte in the sample.

22 Claims, 3 Drawing Sheets

(56) References Cited

U.S. PATENT DOCUMENTS

2008/0280374 A1  11/2008  Potyrailo et al.
2008/0285039 A1  11/2008  Que et al.

FOREIGN PATENT DOCUMENTS

| WO | 2010099805 | 9/2010 |
| WO | 2011050272 | 4/2011 |
| WO | 2011106057 | 9/2011 |

OTHER PUBLICATIONS

Written Opinion in the parent PCT application No. PCT/US2012/066397, dated Feb. 11, 2013.
Stewart et al., "Nanostructured Plasmonic Sensors", Chemical Reviews, Jan. 20, 2008, vol. 108, No. 2, pp. 494-521.
Im et al., "Plasmonic Nanoholes in a Multi-Channel Microarray Format for Parallel Kinetic Assays and Differential Sensing", Analytial Chemistry, Apr. 15, 2009, 81(8), pp. 2854-2859.
Yanik et al., "Seeing Protein Monolayers with Naked Eye through Plasmonic Fano Resonances", PNAS, vol. 108 No. 29, Jul. 19, 2011, pp. 11784-11789.

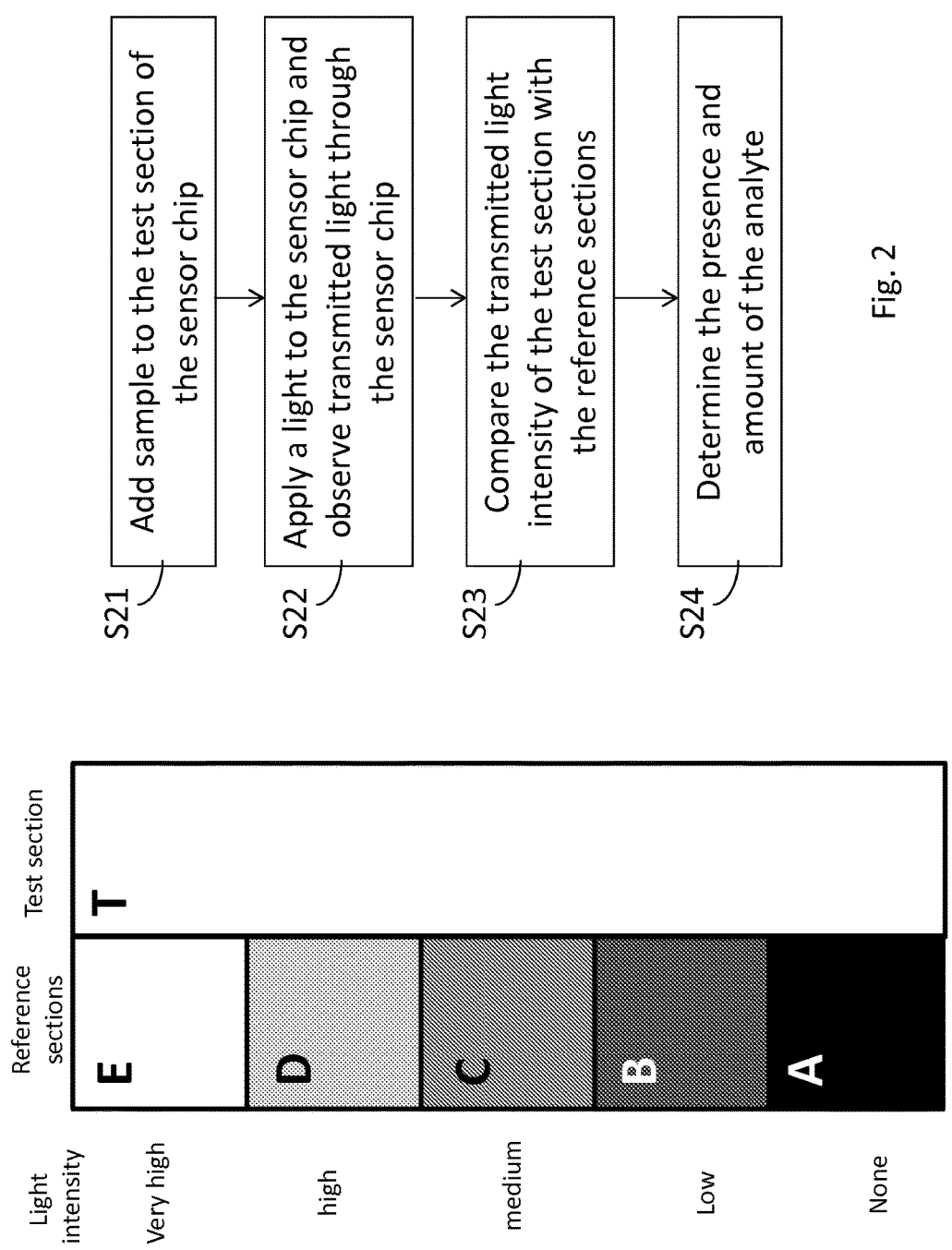

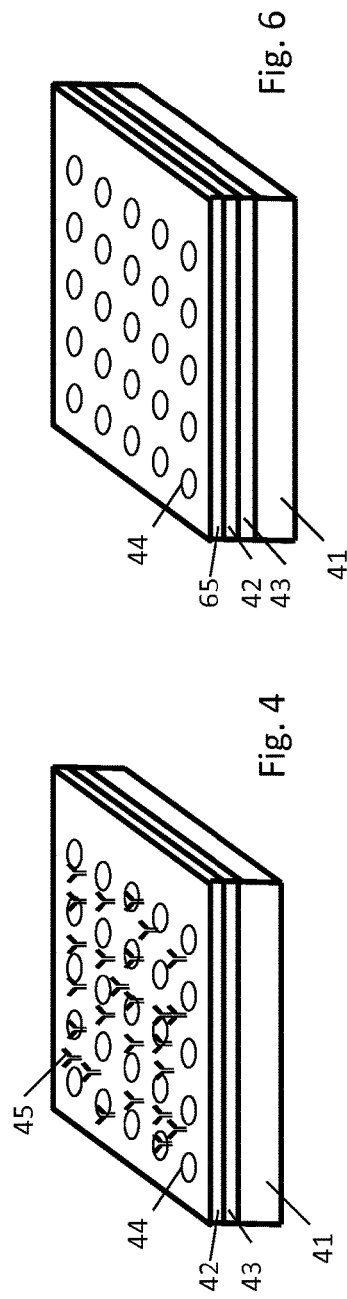
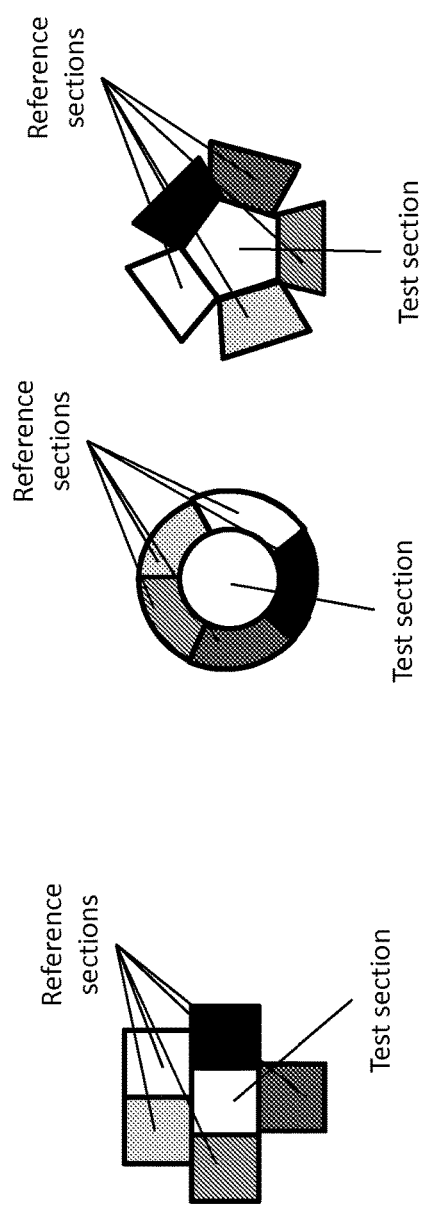

NANOHOLE SENSOR CHIP WITH REFERENCE SECTIONS

BACKGROUND OF THE INVENTION

Field of the Invention

This invention relates generally to the field of plasmonic nanostructure sensors and methods for detection and quantification of biological, chemical, or biochemical molecules and compounds through plasmonic Fano resonance signaling.

Description of the Related Art

The ability to detect biological, chemical, and biochemical analytes such as proteins, DNA, RNA, enzymes, viral particles, prions, toxins, and non-biologic small molecules such as drugs and drug metabolites is extremely important in life sciences research as well as in personalized medicine. Such detection in point-of-care diagnostics allows early detection of analytes associated with a particular disease state or predisposition which can then be followed through with the appropriate treatment. Likewise, the detection of chemical molecules and small molecule drugs and drug metabolites has a wide range of ramifications both within and outside the clinic.

Traditionally, such detection has been limited by the use of systems and equipment requiring labels such as fluorescent dyes and radiolabels that can change conformation of the analyte and often require time-consuming steps and substantial and specialized equipment. Further, traditional detection techniques such as immunoassays, DNA sequencing, polymerase chain reaction (PCR), and cell and tissue-culture are not conducive to point-of-care diagnostics in that the equipment for carrying out these extensive tests are not readily available in a physician's office, and the results from the tests take days if not weeks to obtain.

Recently, plasmonic biosensors using nanostructures for detection of specific biomolecules and chemicals with the naked eye have been developed, which are considered a breakthrough for point-of-care diagnostics. See U.S. Pat. No. 7,612,883, US 2008/0280374 A1, US2008/0285039 A1, US 2008/0278728 A1, WO 2011/106057, WO 2010/099805, WO 2008/136734, and WO 2008/039212. The art describes how nanostructure biosensor platforms can be constructed using substrates, metal films, periodically arranged nanoelements (particularly nanoholes), and capture agents such as ligands that can bind specific analytes.

The plasmonic sensor detection technique essentially employs a light source with a plasmonic nanostructure sensor that contains a test portion for testing a particular analyte, and utilizes certain optical transmission effects of the nanoholes that can be detected with the naked eye, or with a simple detection mechanism. These techniques generally rely on various surface photonic phenomenon observed in nanoholes due to light and/or electromagnetic waves trapped at the metal/dielectric interfaces of these nanostructure platforms.

One such biosensor device is based on asymmetric Fano resonances, a wave phenomenon, that is observed in plasmonic nanoholes. Yanik, et al., Seeing Protein Monolayers With Naked Eye Through Plasmonic Fano Resonances, Proceedings of the National Academy of Sciences of the United States of America (PNAS), vol. 108, no. 29, 11784-789 (Jul. 19, 2011). A Fano resonance is a type of resonant scattering phenomenon that gives rise to an asymmetric line-shape. Sharp plasmonic Fano resonances in nanohole sensors result in dramatic light intensity changes in response to the slightest excitation in the local environment. This light intensity change can be seen on the biosensor device with the naked eye without use of special optical detection instruments such as cameras and spectrometers.

Specifically, an extremely uniform nanostructure sensor chip containing certain ligands transmits particular wavelengths of light much more strongly than that predicted by classical aperture theory. When a test sample contains a particular analyte that is sought to be detected, the analyte binds to the ligand immobilized on the nanohole sensor chip. The ligand-analyte binding causes a shift in the wavelength of this extraordinary optical transmission (EOT), and the light intensity changes, which can be observed with the naked eye. Biosensor devices exploiting these Fano resonances have been used to directly detect a single monolayer of antibodies with the naked eye, and have far-reaching ramifications in personalized medicine and life science research. Id.

The illustration in FIG. 1 of the above-mentioned Yanik reference outlines how extremely uniform nanohole sensor can be fabricated using lift-off free evaporation (LIFE) nanolithography. FIG. 5 of the same reference illustrates that the extremely uniform nanohole sensor chip transmits EOT strongly, and that the EOT exhibit a shift in peak wavelength by about 22 nm when an analyte (e.g. mouse IgG antibody) in the test sample binds to capture molecules (e.g. protein A/G) immobilized on the nanohole sensor chip. The transmitted EOT light is filtered by a notch filter (WHM≈10 nm) spectrally tuned to the plasmonic resonances peak. As a result, the shift in peak wavelength causes a dramatic change in light intensity after the notch filter. Thus, an unfunctionalized control sensor exhibits a particular light intensity when viewed with a simple light source. A sample which does not contain the particular analyte that is sought to be detected exhibits a similar light intensity as the control because of non-specific binding. A sample that contains the analyte which is sought to be detected exhibits a different light intensity than the control because of the analyte-antibody specific binding. The differences in the light intensity can be distinguished with the naked eye.

SUMMARY OF THE INVENTION

While the detection ability of conventional nanohole biosensors is remarkable, existing nanohole biosensors do not allow quantification of the test analyte. Hence, while one can determine whether a particular analyte is present, it is difficult to determine how much of the analyte is in the sample. Quantification is extremely important both to the clinician as well as the researcher in that it helps distinguish disease from non-disease states, and further allows fine-tuning of the diagnosis and treatment plan. For example, the presence of certain analyte in a blood sample may not necessarily indicate a particular disease, but excessive amounts of the analyte may be indicative of a health condition, such as chronic inflammation, immune-mediated disease, or stress response. As another example, measuring and charting C-reactive protein values can be useful in determining disease progression or the effectiveness of treatments. Furthermore, monitoring CD4+ T-cell counts is important for AIDS treatment plans and prognosis.

Accordingly, the present invention is directed to a device and a method for detecting and assessing the quantity of an analyte in a test sample comprising a plasmonic nanohole sensor chip with a test section and a reference section that allows quantification of the test analyte, thus obviating one or more problems due to limitations and disadvantages of the related art.

To achieve these and other advantages and in accordance with the purpose of the present invention, as embodied and broadly described, an embodiment of the present invention discloses a device for detecting and assessing the quantity of an analyte in a test sample, comprising a plasmonic nanohole sensor chip, said chip comprising first and second sections, wherein the first section comprises a test section, upon which capture agents for the analyte are immobilized, and the second section comprises a reference section, upon which capture agents conjugated with known quantities of the analyte are immobilized.

Another embodiment of this invention discloses a device for detecting and assessing the quantity of an analyte in a test sample, comprising a plasmonic nanohole sensor chip, comprising a test section and a plurality of reference sections, wherein antibodies to the analyte are immobilized upon the test section of the chip, and wherein a plurality of antibody-analyte conjugates containing different known quantities of the analyte are immobilized in each reference section.

Another embodiment of this invention discloses a method for detecting and assessing the quantity of an analyte in a test sample using a plasmonic nanohole sensor chip with a first test section and a plurality of reference sections, wherein antibodies to the analyte are immobilized upon the test section of the chip, and wherein a plurality of antibody-analyte conjugates containing different quantities of the analyte are immobilized in each reference section, comprising the steps of placing a sample on the test section, allowing the sample to flow and react with the antibodies within the test section, applying a light source to the nanohole sensor chip, and comparing the light intensity exhibited by the test section with the light intensities exhibited in each reference section to estimate the quantity of analyte in the sample.

Additional features and advantages of the invention will be set forth in the descriptions that follow and in part will be apparent from the description, or may be learned by practice of the invention by those of ordinary skill in the art. The objectives and other advantages of this invention that will be realized and attained by the device and method will be particularly pointed out in the written description and claims thereof as well as the appended drawings.

It is to be understood that both the foregoing summary and the following detailed description are exemplary and included to provide a basic understanding of some aspects and features of the invention. They are not an extensive overview of the invention, nor are intended to particularly delineate the scope of the invention. Rather, they provide some concepts of the invention in a simplified manner as a further explanation of the invention as claimed.

BRIEF DESCRIPTION OF THE DRAWINGS

FIG. 1 schematically depicts a nanohole sensor chip with reference sections and a test section according to an embodiment of the present invention.

FIG. 2 schematically illustrates a process of quantifying an analyte using the nanohole sensor chip.

FIG. 4 schematically illustrates the structure of a test section of a nanohole sensor chip.

FIG. 5a-c depicts the different shapes in which the reference sections and test section can be configured in a nanohole sensor chip according to alternative embodiments of the present invention.

FIG. 6 schematically illustrates the structure of a reference section of a nanohole sensor chip according to an alternative embodiment of the present invention.

DETAILED DESCRIPTION OF THE PREFERRED EMBODIMENTS

Figure 3:
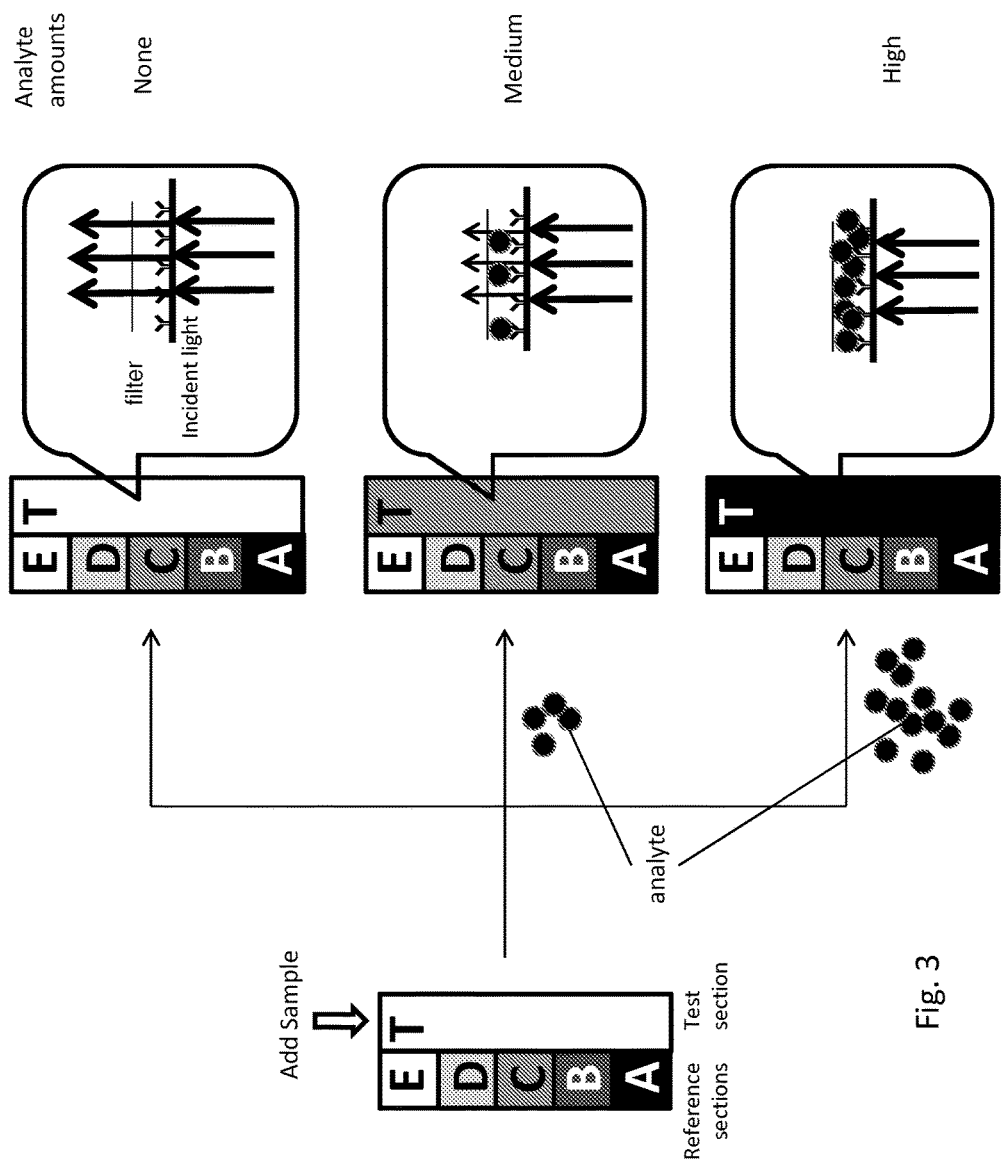
FIG. 3 schematically shows the in light intensity produced by antibody-analyte binding on the test section and the various reference sections of the nanohole sensor chip of FIG. 1.

As described above, an embodiment of this invention is directed to a plasmonic nanosensor device generally comprising one or more reference sections and a test section that allows quantification as well as detection of particular analytes using a simple light source and the naked eye. In particular, in one embodiment, the device comprises a plasmonic nanohole sensor chip, said chip comprising first and second sections, wherein the first section comprises a test section upon which capture agents to an analyte are immobilized, and the second section comprises one or more reference sections upon which capture agents conjugated with known quantities (which may include zero) of the analyte are immobilized. In another embodiment of the invention, the plasmonic nanohole sensor chip comprises a plurality of reference sections and a test section. In yet another embodiment of this invention, a method for quantifying analytes using a plasmonic nanohole sensor chip with one or more reference sections and a test section is disclosed. In a further embodiment of this invention, a method for quantifying analytes using a plasmonic nanohole sensor chip with a test section and a plurality of reference sections is disclosed.

In one embodiment of this invention, the nanohole sensor chip is composed of a substrate, a metal film disposed upon the substrate, an adhesion layer between the substrate and the metal film, a plurality of periodically spaced nanoholes disposed on said substrate, antibodies (or other capture agents) for an analyte sought to be detected immobilized on the metal film in a test section of the chip, and antibody-analyte conjugates with at least one known quantity (which may include zero) of the analyte to be detected immobilized on the metal film in a reference section of the chip. A notch filter or band-pass filter with a narrow rejection or transmission band (about 10 nm) spectrally tuned to the plasmonic resonances peak is disposed adjacent the substrate on the same side as the capture agents. A light illuminates the sensor chip from the side opposite the notch filter, and the transmitted light is observed from the side of the filter. When a particular analyte sought to be detected is present in the sample placed on the test section of the nanohole sensor chip, the analyte reacts with or binds to the antibodies on the test section, producing a shift in the wavelength of the extraordinary optical transmission (EOT), and accordingly, a light intensity change after the notch filter. The light change is compared between the test section and the reference section(s). Comparison of the light intensity in the test section against the different reference sections allows one to determine the quantity of the analyte sought to be detected.

A device in accordance with an embodiment of the present invention is shown in FIG. 1, which illustrates a rectangular plasmonic nanohole sensor chip with a test section and a plurality of reference sections. Specifically, five reference sections A to E are shown in this particular sensor chip. The reference sections are aligned side-by-side to the test section of the sensor chip. The first reference section from the top, (E), contains no antibody-analyte conjugates and serves as a control. The second reference section from the top, (D), contains a small amount of analyte conjugated with an antibody. The third reference section in the middle, (C), contains a medium quantity of analyte conjugated with an antibody. The fourth reference section from the top, (B), contains a high quantity of analyte conjugated with an antibody. And, the fifth reference section from the top, (A), contains a very high quantity of analyte conjugated with the antibody.

When the incident light source is applied to the nanohole sensor in FIG. 1, one can see the light intensity differences among the reference sections with the naked eye. For example, the control (E) contains only antibodies, and no antibody-analyte conjugate. When incident light is applied, the wavelengths pass through the filter, and can be seen as very high EOT. Reference section (D) exhibits a high light intensity when viewed with an incident light source. Reference section (C) exhibits a middle light intensity. Reference section (B) exhibits a low light intensity, and reference section (A) exhibits very low or no light intensity, corresponding to the high quantity of analyte in the antibody-analyte conjugate in that reference section.

In a method according to an embodiment of the present invention, a sample is added to the test section (T) of the sensor chip as shown in FIG. 3 and allowed to flow. If the sample contains the analyte that is sought to be detected by the sensor, it will react or bind to the antibodies immobilized on the test section of the chip, and the shift in Fano resonance wavelength in the nanohole chip coupled with the notch filter or band-pass filter (see FIG. 3) will exhibit a light intensity that will be different from the control (no analyte). The light intensity exhibited by the antibody-analyte binding in the test section (T) of the chip is then compared with that exhibited by the antibody-analyte conjugates in the reference sections A to E to assess the amount of analyte present in the sample. If, for example, the sample contains approximately the same amount of analyte as in a particular reference section shown in FIG. 1, it will exhibit the same light intensity as that reference section. Three examples are shown in FIG. 3, to illustrate the situation where the sample contains no analyte, a medium amount of analyte similar to that provided in reference section C, and a high amount of analyte similar to that provided in reference section A.

If the sample contains an analyte that is not the same as that contained in any particular reference section, the light intensities from the sections can still be compared to estimate the amount of analyte in the sample. For example, the analyte in the sample may be between the amounts in reference sections (B) and (C), and will exhibit a light intensity that is somewhere between those exhibited by those sections. This allows the researcher or clinician to estimate that the quantity of analyte in the sample is somewhere between the amounts in (B) and (C).

FIG. 2 summarizes the steps of above-described process of using the nanohole sensor chip to determine the amount of analyte present in a sample. Step S21: Add a sample to the test section of the sensor chip and allow it to react. Step S22: Apply a light to the sensor chip and observe the transmitted light through the chip. Step S23: Compare the transmitted light intensity of the test section with that of the reference sections. Step S34: Determine the presence and amount of the analyte based on the comparison.

In one embodiment of this invention, shown in FIG. 4, the plasmonic nanohole sensor chip is composed of a substrate 41, a metal film 42 disposed upon the substrate, a plurality of nanoelements or nanoholes 44 arranged in a period pattern on a substrate, and an adhesion layer 43 between the metal film and the substrate. The capture agents 45, such as antibodies or antibody fragments, are immobilized on the metal film 42. The filter is not shown in FIG. 4 but is shown in FIG. 3. Suitable materials for the substrate include, but are not limited to, silicon dioxide, silicon nitride, glass, quartz, magnesium fluoride, calcium fluoride, zinc selenide (ZnSe), germanium, or a polymer. The metal film may be composed from a noble metal, a transition metal, or an alkali metal, including but not limited to, gold, palladium, rhodium, silver, osmium, iridium, platinum, titanium, aluminum, or any other combination thereof.

The thickness of the metal film disposed upon the substrate may be anywhere from 50 to 500 nm thick, and preferably, 75 to 200 nm thick. The dimension of the nanoholes in one embodiment of this invention is approximately 10-1000 nm. In a preferred embodiment of the invention, the nanoholes are 50-300 nm. The plurality of nanoholes is arranged in a periodic pattern separated by a periodicity of between 100 to 1000 nm, preferably, 400-800 nm. The adhesion layer between the metal film and the substrate should be less than 50 nm, and may be composed of titanium, chromium, or any combination thereof. In one preferred embodiment, the adhesion layer is less than 25 nm, and in another preferred embodiment, the adhesion layer is less than 15 nm.

The metal film is functionalized with one or more capture agents for detecting a particular analyte, including but not limited to, an antibody, an antibody fragment, a receptor, a recombinant fusion protein, a nucleic acid molecule, or any combination thereof. For high density immobilization of capture agents on the metal film, a solid support may be used between the metal film and capture agents. Suitable solid supports include, but are not limited to, a hydrophilic polymer, carboxyl methyl dextran (CMD), polyethylene glycol (PEG), poly(acrylic acid), and poly(methacrylic acid).

The test section and the reference sections of the nanohole sensor chip may be configured in a number of shapes, alignments, and sizes, so long as at least each of the reference section(s) and the test section are in contact with or in the vicinity to each other. In one embodiment, the test section may be surrounded by a plurality of reference sections. In another embodiment, the test section may surround the plurality of reference sections. In a further embodiment, the test section and the reference section(s) may be aligned side-by-side on the chip. Hence, the test and reference section(s) may be configured in various shapes, including, but not limited to, triangles, rectangles, circles, pentagons, and trapezoids. FIGS. 5a-5c illustrate some examples of the various shapes in which the test and reference sections of the nanohole sensor can be configured. It is preferred that the size of the test section and the reference section(s) be as small as an area as possible yet still allow detection of an analyte. Accordingly, in one embodiment of the invention, each test section and each reference section is approximately less than 1000 $mm^2$. In another embodiment of the invention, each test section and each reference section is approximately less than 100 $mm^2$. In a preferred embodiment of the invention, each test section and each reference section is approximately less than 10 $mm^2$.

The reference section(s) of the device according to embodiments of the present invention may be constructed by, but is not limited to, immobilizing known amounts of analytes to a nanostructure sensor. The structure of such reference sections may have the same or similar structure as that shown in FIG. 4, with analytes bound to the capture agents 45. Other types of reference sections may use, for example, certain filters, dielectric layers, and ion solutions that control dielectric constants. For example, instead of capture molecules and analytes, a dielectric layer can be formed on the metal film using self-assembled monolayer and surface chemistry. Possible dielectric layers include, but are not limited to, various optically transparent inorganic, natural or synthetic polymers, preferably $SiO_4$ or $TiO_2$. Alternatively, an ion solution can be placed on the metal film and contained with a container made from the material which has high light transparency such as glass, PMMA, acrylic resin. The different reference sections A-E may be separated by different containers. Generally, any ion solution may be used, including but not limited to, NaCl, KCl, $MgCl_2$, $CaCl_2$, $NaHCO_3$. This structure is schematically illustrated in FIG. 6, where layer 65 represents the dielectric layer or ion solution layer.

The dielectric layers or ion solutions cause changes in the dielectric constants of the metal film surface, which in turn causes shifts in the resonance wavelength of the transmitted EOT light. As a result, the light intensity observed after the notch filter or band pass filter is changed. The observer light intensity after the filter depends on the density of dielectric layer or concentration of ion solution. Thus, different reference sections A-E are provided with different densities of dielectric layer or different concentrations of ion solution such that the light intensities for these reference sections correspond to those produced when known amounts of analyte are immobilized on the sensor.

Suitable filters that may be used as the reference sections include, but are not limited to, band-pass filter and notch filter for light intensity control.

The test section of the nanohole sensor chip may be constructed by immobilizing one or more capture agents for detecting particular analytes, including but not limited to, an antibody, an antibody fragment, a receptor, a peptide, a recombinant fusion protein, an enzyme, a nucleic acid molecule, a small organic molecule, or any combination thereof, upon the nanohole sensor.

The analyte sought to be detected and quantified using the nanohole sensor chip disclosed herein may be any biomolecule, compound, or chemical formulation, including but not limited to, a eukaryotic cell, a eukaryotic cellular component, a prokaryote, a prokaryotic cellular component, a viral particle, a protein, an oligonucleotide, a prion, a toxin, an enzyme, a hormone, a recombinant cell, a recombinant protein, a non-biologic small molecule, such as a drug, or drug metabolite, and/or any combination thereof. Samples that may be tested for presence of one or more analytes described above include, but are not limited to, cells, organisms such as bacteria and viruses, lysed cells or organisms, cellular extracts, nuclear extracts, components of cells or organisms, extracellular fluid, media in which cells or organisms are cultured in vitro, blood, plasma, serum, gastrointestinal sections, homogenates of tissues or tumors, synovial fluid, feces, saliva, sputum, cyst fluid, urine, amniotic fluid, cerebrospinal fluid, peritoneal fluid, lung lavage fluid, semen, lymphatic fluid, tears, pleural fluid, nipple aspirates, breast milk, external sections of skin, respiratory, intestinal, and genitourinary tracts, and prostatic fluid.

In one embodiment of the invention, the reaction of the analyte and the capture agent in the test section is performed by adding the sample to the test section of the nanohole sensor chip. Reaction conditions, including static reaction, shaking, and flow reaction may be utilized. Reaction temperatures between 4 and 40° C., preferably 25 to 37° C., may be utilized.

The light source used to observe the light intensity changes in the nanohole sensor chip can be any polychromatic illumination device, a broad spectral light source, or a monochromatic light source including but not limited to, a gas discharge lamp (Halogen light), a gas arced pulse lamp, an incandescent lamp, LED, as well as natural light. It is preferred that the incident light be in the UV-visible-IR spectral range with a UV range of 10 to 400 nm, a visible range of 380 to 750 nm, and an IR range of 750-100,000 nm (preferably, 750 to 1000 nm). The light intensity changes produced by the shift of Fano resonance wavelength coupled with the band-pass or notch filter in the nanohole sensor can be detected by the naked eye. However, detection and quantification of the analyte through comparison of different light intensity changes is not limited to viewing with the naked eye. Rather, mobile phone cameras, microscopes, cameras, and photometers may be used for accurate detection and comparison of the light intensity changes.

It will be apparent to those skilled in the art that various modification and variations can be made in the device and method of the present invention without departing from the spirit or scope of the invention. Thus, it is intended that the present invention cover modifications and variations that come within the scope of the appended claims and their equivalents.

What is claimed is:

1. A device for detecting and assessing a quantity of an analyte in a test sample, comprising a plasmonic nanohole sensor chip which includes a substrate defining a plurality of nanoholes and a metal film disposed on the substrate, said chip comprising first and second sections,
   wherein the first section comprises a test section, upon which capture agents for the analyte are immobilized, and
   the second section comprises at least three reference sections, upon which capture agents conjugated with at least three different known quantities of the analyte are immobilized, respectively.

2. The device of claim 1, wherein the test section and the at least three reference sections are arranged adjacent each other.

3. The device of claim 1, wherein the nanohole sensor chip further comprises:
   an adhesion layer between the metal film and the substrate,
   wherein the capture agents and the capture agents conjugated with the analyte are immobilized on the metal film, and
   wherein the plurality of nanoholes are arranged in a periodic pattern.

4. The device of claim 3, wherein the substrate is made of silicon dioxide, silicon nitride, glass, quartz, magnesium fluoride, calcium fluoride, zinc selenide, germanium, or a polymer.

5. The device of claim 3, wherein the metal film includes a noble metal, a transition metal, or an alkali metal, or combinations thereof.

6. The device of claim 3, wherein a thickness of the metal film is from 50 to 500 nm.

7. The device of claim 3, wherein a dimension of the nanoholes is from 10 to 1000 nm.

8. The device of claim 3, wherein a periodicity of the period pattern of the nanoholes is from 100 to 1000 nm.

9. The device of claim 3, wherein the adhesion layer is less than 50 nm thick, and wherein the adhesion layer includes titanium or chromium, or combinations thereof.

10. The device of claim 3, wherein the nanohole sensor chip further comprises a solid support over the metal film, wherein the capture agents and the capture agents conjugated with the analyte are immobilized on the solid support.

11. The device of claim 3, wherein the solid support include a hydrophilic polymer, carboxyl methyl dextran (CMD), polyethylene glycol (PEG), poly(acrylic acid), or poly(methacrylic acid).

12. The device of claim 3, further comprising a notch filter or band-pass filter disposed adjacent the nanohole sensor chip on a same side as the capture agents.

13. The device of claim 1, wherein the capture agents include antibodies, antibody fragments, receptors, peptides, recombinant fusion proteins, enzymes, nucleic acid molecules, or small organic molecules, or combinations thereof.

14. The device of claim 1, wherein the analyte includes eukaryotic cells, eukaryotic cellular components, prokaryotes, prokaryotic cellular components, viral particles, proteins, oligonucleotides, prions, toxins, enzymes, hormones, recombinant cells, recombinant proteins, or non-biologic small molecules, or combinations thereof.

15. A method for quantifying analytes using a plasmonic nanohole sensor chip which includes a substrate defining a plurality of nanoholes and a metal film disposed on the substrate, the sensor chip comprising a test section, upon which capture agents for the analyte are immobilized, and at least three reference sections, upon which capture agents conjugated with at least three different known quantities of the analyte are respectively immobilized, the method comprising:
   adding a sample to the test section of the sensor chip;
   applying a light to the sensor chip;
   comparing intensities of light transmitted through the test section and the reference sections of the sensor chip; and
   determining a presence and amount of the analyte in the sample based on the comparison.

16. The method of claim 15, wherein the comparing step is performed by naked eyes.

17. The method of claim 15, wherein the nanohole sensor chip further comprises:
   an adhesion layer between the metal film and the substrate,
   wherein the capture agents and the capture agents conjugated with the analyte are immobilized on the metal film, and
   wherein the plurality of nanoholes are arranged in a periodic pattern.

18. A plasmonic nanohole sensor chip for detecting and assessing a quantity of an analyte in a test sample, comprising:
   a substrate, the substrate defining a plurality of nanoholes arranged in a periodic pattern;
   a metal film disposed on the substrate;
   an adhesion layer between the metal film and the substrate;
   capture agents for the analyte immobilized on a first section of the metal film; and
   a dielectric layer or an ion solution placed on a second section of the metal film, the second section including at least three reference sections, wherein in different ones of the at least three reference sections, the dielectric layer has different densities or the ion solution has different concentrations.

19. The plasmonic nanohole sensor chip of claim 18, wherein the first section and the at least three reference sections are arranged adjacent each other.

20. The device of claim 2, wherein the at least three sections are arranged in an order of their quantities of the analyte to be used as a scale.

21. The method of claim 15, wherein the at least three sections are arranged in an order of their quantities of the analyte to be used as a scale.

22. The plasmonic nanohole sensor chip of claim 19, wherein the at least three sections are arranged in an order of the densities of the dielectric layer or the concentrations of the ion solution to be used as a scale.

* * * * *